United States Patent
McBrayer et al.

[11] Patent Number: 5,779,701
[45] Date of Patent: Jul. 14, 1998

[54] BIPOLAR ENDOSCOPIC SURGICAL SCISSOR BLADES AND INSTRUMENT INCORPORATING THE SAME

[75] Inventors: Michael Sean McBrayer, Miami; Juergen Andrew Kortenbach, Miami Springs, both of Fla.

[73] Assignee: Symbiosis Corporation, Miami, Fla.

[21] Appl. No.: 429,596

[22] Filed: Apr. 27, 1995

[51] Int. Cl.$^6$ .................................................. A61B 17/39
[52] U.S. Cl. ........................... 606/46; 606/48; 606/50
[58] Field of Search .......................... 606/45, 46, 48–52

[56] References Cited

U.S. PATENT DOCUMENTS

| | | |
|---|---|---|
| 3,651,811 | 3/1972 | Hildebrandt et al. |
| 4,418,692 | 12/1983 | Guay. |
| 4,646,734 | 3/1987 | Cabrera et al. ............... 606/2 |
| 4,850,353 | 7/1989 | Stasz et al. ............ 128/303.14 |
| 4,862,890 | 9/1989 | Stasz et al. ............ 128/303.14 |
| 4,958,539 | 9/1990 | Stasz et al. ............... 76/104.1 |
| 4,962,766 | 10/1990 | Herzon ........................ 128/741 |
| 5,007,908 | 4/1991 | Rydell . |
| 5,120,596 | 6/1992 | Yamada ........................ 428/216 |
| 5,324,289 | 6/1994 | Eggers ........................... 606/48 |
| 5,330,471 | 7/1994 | Eggers ........................... 606/48 |
| 5,342,381 | 8/1994 | Tidemand ..................... 606/52 |
| 5,356,408 | 10/1994 | Rydell .......................... 606/48 |
| 5,562,659 | 10/1996 | Morris ........................... 606/41 |

FOREIGN PATENT DOCUMENTS

| | | | |
|---|---|---|---|
| 0624348 | 11/1994 | European Pat. Off. ....... 606/51 |
| 2680314 | 8/1991 | France ........................... 606/51 |

*Primary Examiner*—Lee S. Cohen
*Attorney, Agent, or Firm*—Finnegan, Henderson, Farabow, Garrett & Dunner, L.L.P.

[57] ABSTRACT

Endoscopic bipolar scissor blades are formed in a laminate assembly of an outer electrically conductive layer, an intermediate electrically insulating layer, and an inner face layer which is a coating of titanium dioxide, chromium dioxide, or zirconium dioxide. In one embodiment, the conductive layer is a metal blade, while the insulating material is a ceramic which is fixed to the metal blade. In a second preferred embodiment, the insulating layer and the inner face layer are applied simultaneously by coating the metal blade with a mixture of ceramic and titanium dioxide, chromium dioxide, or zirconium dioxide. In a third embodiment, the insulating layer is a molded ceramic blade, and the electrically conductive layer is metalized or otherwise fixed to the ceramic blade. In all embodiments, the cutting edges and shearing surfaces are insulated from the electrodes, and no short circuit can form between the electrodes even though the cutting edges and shearing surfaces are metal. Each of the embodiments may be applied to straight or curved scissor blades. A bipolar endoscopic instrument utilizing blades according to the invention is also disclosed.

43 Claims, 6 Drawing Sheets

5,779,701

BIPOLAR ENDOSCOPIC SURGICAL SCISSOR BLADES AND INSTRUMENT INCORPORATING THE SAME

BACKGROUND OF THE INVENTION

1. Field of the Invention

The present invention relates generally to endoscopic surgical instruments. More particularly, the invention relates to an endoscopic surgical instrument having end effectors made out of a combination of conductive and non-conductive materials. The invention has particular use with respect to bipolar endoscopic cautery. For purposes herein, the term "endoscopic instruments" is to be understood in its broadest sense to include laparoscopic, arthroscopic, and neurological instruments, as well as instruments which are inserted through an endoscope.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like. Because of their very small size and the requirements of strength and/or sharpness, end effectors are difficult to manufacture and are typically formed of forged stainless steel. As such, they form an expensive portion of the endoscopic instrument.

Modern endoscopic procedures often involve the use of electrocautery, as the control of bleeding by coagulation during surgery is critical both in terms of limiting loss of blood and in permitting a clear viewing of the surgical site. As used herein, cautery, electrocautery, and coagulation are used interchangeably. Several types of electrocautery devices for use in endoscopic surgery are described in the prior art. Monopolar electrosurgical instruments employ the instrument as an electrode, with a large electrode plate beneath and in contact with the patient serving as the second electrode. High frequency voltage spikes are passed through the instrument to the electrode (i.e., end effector) of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it is has been observed that monopolar cautery can result in excessive tissue damage due to the arcing between the end effector and the tissue.

In order to overcome the problems associated with monopolar cautery instruments, bipolar instruments have been introduced. In bipolar electrosurgical instruments, two electrodes which are closely spaced together are utilized to contact the tissue. Typically, one end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

Various endoscopic instruments with cautery capability are known in the art. U.S. Pat. No. 4,418,692 to Guay, for example, discloses a device for use in laparoscopic tubal cauterization for blocking the Fallopian tubes of a patient. The device comprises a substantially tubular body member having a spring-biased piston slidably mounted therein. A pair of electrodes (either monopolar or bipolar) are disposed to grasp living tissue when the piston is in a first position biased by the spring and to release the tissue when a button is pressed which moves the piston into a second position. The device includes a circuit breaker which interrupts current flowing to the electrodes when the piston is in the second position. When the electrodes grasp the tissue, however, current is supplied to the entire surface of the electrode, that is, both the grasping surface and the outer non-grasping surface.

Another electrosurgical instrument for use in combination with an endoscope is disclosed in U.S. Pat. No. 5,007,908 to Rydell for "Electrosurgical Instrument Having Needle Cutting Electrode and Spot-Coag Electrode". Rydell's device includes an elongated flexible tubular member with a plurality of lumens. The distal end of the tubular member is provided with a bullet shaped ceramic tip covered with a conductive layer and having an opening coupled to a first one of the lumens. The conductive layer is coupled to a conductor which extends through a second one of the lumens to an electrical source. A second conductor, also coupled to the electrical source is slidable through the first lumen by a plunger. The two electrodes form a bipolar pair. In a second embodiment, the conductive layer on the ceramic tip is split by an insulating gap and both halves of the tip form a bipolar pair of electrodes. As with the Guay device, above, substantially the entire distal surface of Rydell's device serves as an electrode when energized.

Several hemostatic bipolar electrosurgical scissors have also been described. U.S. Pat. No. 3,651,811 to Hildebrandt describes a bipolar electrosurgical scissors having opposing cutting blades forming active electrodes. The described scissors enables a surgeon to sequentially coagulate the blood vessels contained in the tissue and then to mechanically sever the tissue with the scissor blades. In particular, with the described bipolar electrosurgical scissors, the surgeon must first grasp the tissue with the scissor blades, energize the electrodes to cause hemostasis, de-energize the electrodes, and then close the scissor blades to sever the tissue mechanically. The scissors are then repositioned for another cut accomplished in the same manner. With the bipolar electrosurgical scissors of Hildebrandt, the surgeon cannot maintain the electrodes in a continuously energized state because the power supply would be shorted out and/or the blades damaged if the blades are permitted to contact each other while energized.

The disadvantages of the bipolar scissors of Hildebrandt are overcome by the disclosure in U.S. Pat. Nos. 5,324,289 and 5,330,471 to Eggers. In its preferred embodiment, the bipolar electrosurgical scissors of Eggers comprise a pair of metal scissor blades which are provided with an electrically insulating material interposed between the shearing surfaces of the blades so that when the scissor blades are closed, the metal of one blade never touches the metal of the other blade; i.e., the insulating material provides the cutting edge and the shearing surface. With the arrangement provided by Eggers, a cautery current will pass from the top back edge of the bottom metal blade through the tissue which is to be cut and to the bottom back edge of the top metal blade directly in advance of the cutting action. As the scissors are gradually closed, the hemostasis preferentially occurs at a location just in advance of the cutting point which itself moves distally along the insulated cutting edges of the blades in order to sever the hemostatically heated tissue. With this arrangement, the scissors may be maintained in a continuously energized state while performing the cutting. The Eggers patent describes various alternative embodiments of the bipolar scissors, including the use of metal blades with only one blade being insulated on its shearing surface, and the use of insulating blades with back surfaces coated with metal.

The disadvantage of scissor blades which have non-conductive cutting edges and shearing surfaces is that they are difficult to operate. The non-conductive surfaces are relatively non-lubricous and do not have the smooth operation and feel of a metal on metal cutting/shearing action.

SUMMARY OF THE INVENTION

It is therefore an object of the invention to provide a pair of scissor blades for a bipolar cauterizing surgical scissors which provide the smooth operation and feel of a metal on metal cutting/shearing action.

It is another object of the invention to provide a pair of scissor blades for a bipolar cauterizing surgical scissors which have shearing surfaces that are insulated from cautery surfaces.

It is also an object of the invention to provide an endoscopic bipolar cauterizing scissors which provide the smooth operation and feel of a metal on metal cutting/shearing action and which may be either curved or flat.

In accord with the objects of the invention, in a first embodiment, the scissor blades of the present invention are comprised of an electrically conductive electrode, an electrically insulating material, and a coating of titanium dioxide, chromium dioxide, or zirconium dioxide. In the first embodiment, the electrode layer is a metal blade which is typically constructed from stainless steel, while the insulating layer is an alumina ceramic which is deposited, bonded, or otherwise fixed on the metal blade, and a titanium dioxide coating is deposited, bonded, or otherwise fixed onto the ceramic and provides the cutting edge and shearing surface. The alumina and titanium dioxide are preferably deposited on a metal scissor blade by thermal spraying of granules at high temperature and standard atmospheric pressure. The titanium dioxide is lubricous and gives the scissor blades the operational feel of metal blades. While titanium dioxide is the preferred coating, chromium dioxide or zirconium dioxide can achieve similar results.

In a second and presently preferred embodiment of the invention, the electrode layer of the scissor blades is a metal blade, and the titanium dioxide is mixed with the alumina ceramic and then applied directly to the conductive electrode. In this preferred embodiment, the ratio by weight of alumina ceramic to titanium dioxide is 87/13, although the ratio can range from 75/5 to 95/5 and still provide the desired insulation and lubricity.

In a third embodiment of the invention, the insulating layer is a ceramic support, with the electrode layer and the titanium dioxide shearing surface layer being deposited, bonded, or otherwise fixed to opposite sides of the ceramic support.

In all embodiments, since the coated cutting edges and preferably at least a portion of the shearing surfaces are insulated from the electrodes, no short circuit can form between the electrodes even though the cutting edge and shearing surface of each scissor blade are in contact with the cutting edge and shearing surface of the other scissor blade.

As the scissor blades are intended for use as part of an endoscopic instrument, each blade is preferably provided with a first hole which receives an axle or clevis pin around which the blades rotate. In addition, each blade is preferably provided with a pin or protrusion extending from a proximal or base portion of the blade. The pins are provided to receive links which couple the blades to an actuator mechanism.

The endoscopic bipolar cautery scissors instrument which utilizes the blades of the invention is substantially as is described in copending U.S. applications Ser. No. 08/284, 793, now U.S. Pat. No. 5,569,2 Ser. No. 08/354,992, and Ser. No. 08/377,156, the complete disclosures of which are hereby incorporated by reference herein, and preferably utilizes a push rod assembly with two conductive push rods which are stabilized and insulated relative to each other. The distal ends of the push rods are coupled to the end effectors by the links. The proximal ends of the push rods extend through the handle and lever of the scissors instrument and present electrical cautery pins onto which a standard bipolar cautery plug can be mated.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
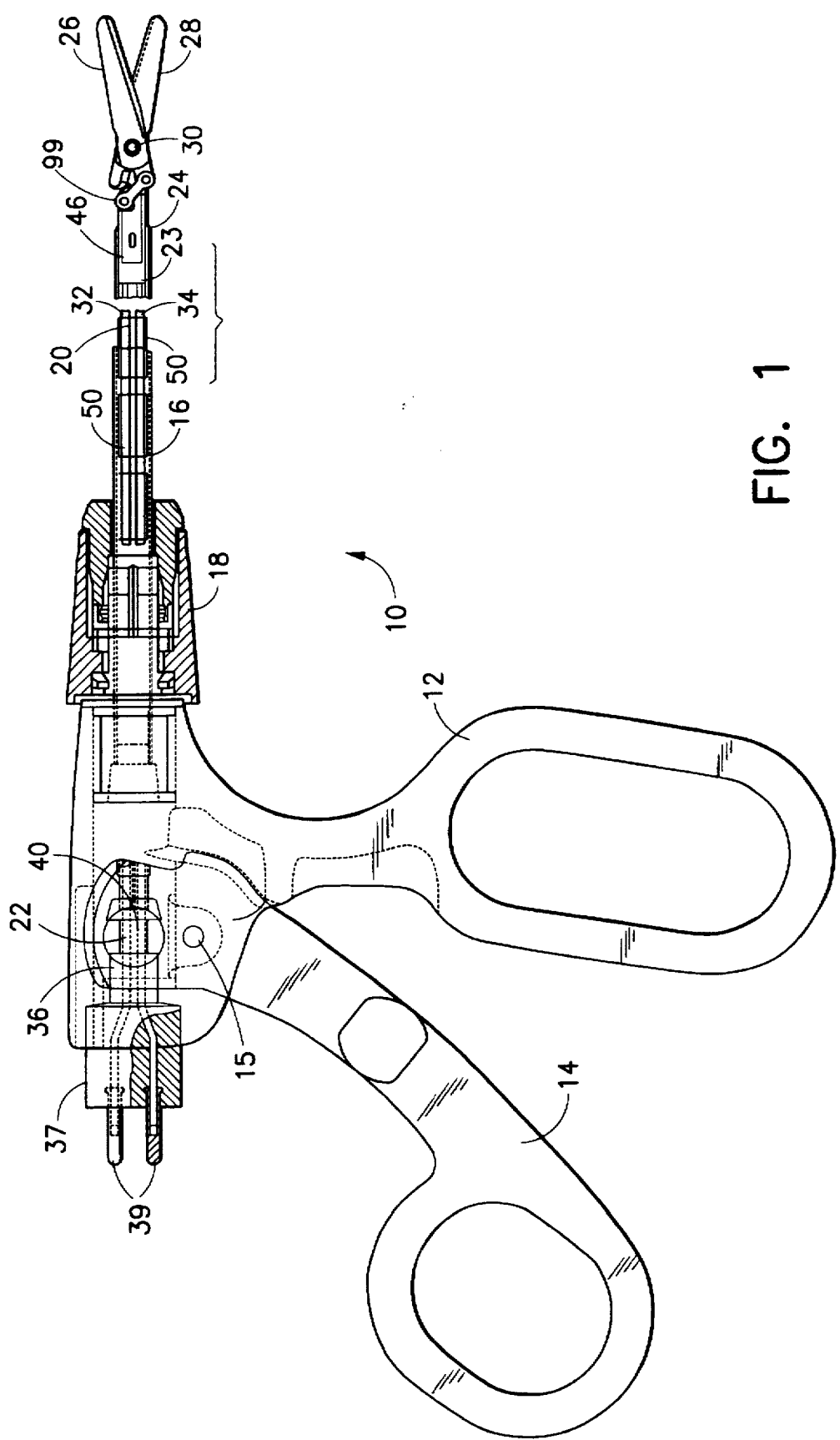
FIG. 1 is a broken side elevation view in partial section of an endoscopic bipolar scissors instrument according to the invention.

Turning now to FIG. 1, an endoscopic bipolar scissors instrument 10 includes a proximal handle 12 with a manual lever actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in previously incorporated copending application Ser. No. 08/284,793. A push rod assembly 20 extends through the hollow tube 16 and is coupled at its proximal end 22 to the manual lever actuator 14 as described in more detail in copending application Ser. No. 08/284,793. The distal end of the tube 16 has an integral clevis 24 within which a pair of scissor blades 26, 28 are mounted on an axle screw 30. The distal end 23 of the push rod assembly 20 is coupled to the scissor blades 26, 28 so that reciprocal movement of the push rod assembly 20 relative to the tube 16 opens and closes the scissor blades 26, 28. It will be appreciated that the reciprocal movement of the push rod assembly 20 relative to the tube 16 is effected by movement of the manual lever actuator 14 relative to the handle 12.

The presently preferred embodiment of the push rod assembly 20 includes a pair of stainless steel rods 32, 34 which are molded into a proximal collar 36 and captured in a distal collar 46. The proximal collar has a radial groove 40 in its distal portion and an increased diameter proximal portion 37 which carries a pair of electrical coupling pins 39 which are electrically coupled to the rods 32, 34. As shown, the pins 39 are spaced farther apart from each other than the rods 32, 34 so as to accommodate a standard cautery connector. The rods 32, 34 are covered with insulating high density polyethylene (HDPE) tubes along substantially their entire length between the proximal and distal collars 36, 46. A plurality of spaced apart polypropylene cylinders 50 are molded about the rods between the proximal collar 36 and the distal collar 46. These cylinders stabilize the rods against helical twisting when the tube 16 is rotated and, by being discontinuous, prevent against warping of the push rod assembly. According to one embodiment, the distal collar 46 is made from two ceramic pieces which are snap fit and bonded to each other. The electrically conductive rods 32, 34 exit the distal collar 46 through opposite sides at substantially right angles. The distal ends of the rods 32, 34 are mechanically and electrically coupled to the respective blades 26, 28 by respective electrically conductive links 99.

Figure 2:
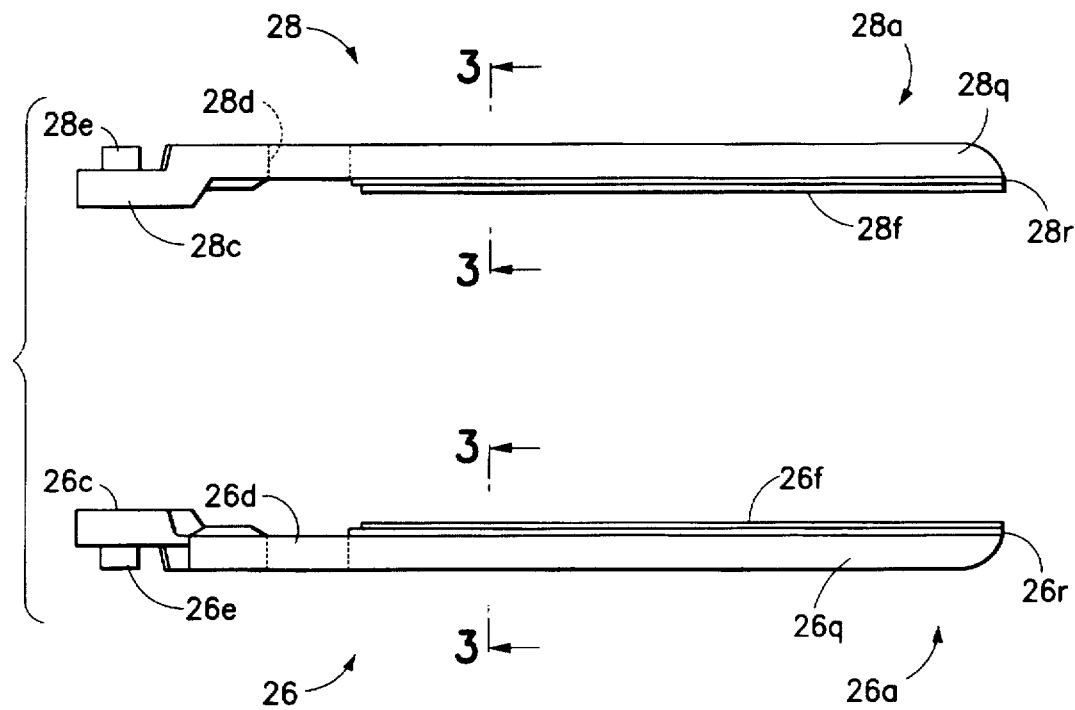
FIG. 2 is an enlarged top view of a first embodiment of straight scissor blades according to the invention.
Figures 3, 4, 5:
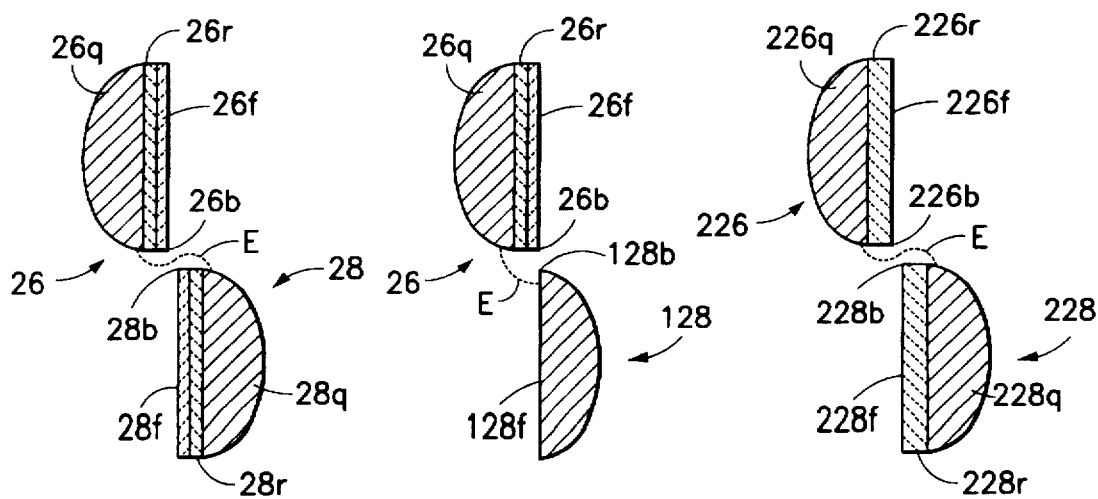
FIG. 3 is a cross sectional view of the scissor blades of FIG. 2 taken along lines 3—3 and shown in their operating positions.
FIG. 4 is a view similar to FIG. 3 but showing one of the scissor blades of FIGS. 2 and 3 in use with a conventional scissor blade in an alternative first embodiment.
FIG. 5 is a view similar to FIG. 3 but showing a second embodiment of straight scissor blades according to the invention.

Referring now to a first embodiment of straight scissor blades according invention seen in FIGS. 2 and 3, the first scissor blade 26 has a distal portion 26a, a lower proximal tang 26c, and a mounting hole 26d therebetween. A connecting lug 26e extends orthogonally outward from the surface of the tang 26c in a first direction. The distal portion 26a includes an lower cutting edge 26b and an inner surface 26f (also called the shearing surface). Behind the inner surface 26f of the first scissor blade is an insulating layer 26r, and a conducting electrode layer 26q. The opposed second scissor blade 28 is configured similarly to the first scissor blade and has a distal portion 28a, an upper proximal tang 28c, and a mounting hole 28d therebetween. A connecting lug 28e extends orthogonally from the surface of the tang 28c in a second direction which is opposite to the first direction mentioned above. The distal portion 28a includes an upper cutting edge 28b and an inner surface 28f. Behind the inner surface 28f of the second scissor blade 28 is an insulating layer 28r, and a conducting electrode layer 28q.

According to the first embodiment shown in FIGS. 2 and 3, both scissor blade assemblies 26 and 28 are laminated assemblies which include a metal support (also called a metal blade support or an outer conductive layer) 26q, 28q, an intermediate electrically insulative layer 26r, 28r and a coated face 26f, 28f defining a shearing surface. It will be appreciated that the Figures herein are not intended to depict the relative thickness of the layers according to any scale and that the thickness of the layers may be exaggerated for illustration purposes. The metal blade supports are preferably stainless steel, although any strong conductive metal may be used. The insulative layer is preferably alumina ($Al_2O_3$), although any suitable ceramic may be used. In accord with the object of providing a metal-on-metal operational feel to the blades, the coated face is preferably a titanium dioxide ceramic ($TiO_2$), although zirconium dioxide ($ZiO_2$) or chromium dioxide ($CrO_2$) ceramics can be used. The coating may be very thin and applied by bonding, chemical vapor deposition, thermal spray, plasma spray or other techniques. It will be appreciated, however, that the faces 26f, 28f are preferably provided with sharpened opposed cutting edges 26b, 28b which may be achieved by sharpening either the insulating layer 26r, 28r, the blade support 26q, 28q, or both either before or after applying the face coating of titanium dioxide. The metal blade supports 26q, 28q form the electrically conductive portions (i.e., the electrodes) of the scissor blades through which cautery current is applied. In this regard, substantially the entire lengths of blade supports 26q, 28q are conductive, including the proximal lugs 26e which make electrical connection with the respective rods 32, 34 via links 99 as described above with reference to FIG. 1. As seen in FIG. 3, the preferential path of current flow "E" is through the metal support portions 26q, 28q of the scissor blades which are insulated from the cutting edges 26b, 28b and the shearing surfaces (faces) 26f, 28f of the blades. Because of this arrangement, cautery and coagulation current may be applied continuously throughout the cutting/shearing procedure since the contact of the cutting edges and shearing surfaces of the blades will not short circuit the device. The titanium dioxide coating on the ceramic insulative layer gives the blades the operational feel of having metal on metal shearing surfaces.

Both the insulative layer and the face layer are preferably applied by thermal spraying of ceramic granules onto the blades. In thermal spraying, such as by a high velocity oxygen fuel (HVOF) system, micron sized powder (granules) of the ceramic is sprinkled into the combustion chamber of a rocket-type engine and is sprayed out of the chamber onto a desired substrate.

From the foregoing, it will be appreciated that in order to achieve the object of preventing the cutting edges and shearing surface from short circuiting the device, it is only necessary that one of the scissor blades be constructed as described above. FIG. 4 shows an alternative to the first embodiment of the invention where one of the blades 26 of the first embodiment is used in conjunction with a conventional scissor blade 128 which is entirely conductive. In this embodiment and in the embodiments described below, similar reference numerals refer to similar elements of the embodiments. As illustrated in FIG. 4, the preferential path of current flow "E" is through the metal support portion 26q of blade 26 to the shearing surface 128f and/or cutting edge 128b of the scissor blade 128.

According to a second and presently preferred embodiment of the invention shown in FIG. 5, scissor blades 226, 228 are formed of a metal blade support 226q, 228q which is substantially the same as the metal blade supports 26, 28 described above. In this embodiment, however, the insulative layer 226r, 228r and the face layer 226f, 228f are applied to the blade supports simultaneously as a single layer containing a mixture of alumina and titanium dioxide. The mixture of alumina and titanium dioxide is preferably applied to the metal blade support by mixing alumina and titanium dioxide granules and by thermal spraying the granules as described above. The weight ratio of the alumina and titanium dioxide in the mixture may range from 75/25 to 95/5 alumina to titanium dioxide, although an 87%/13% is presently preferred to provide the simultaneous insulative and lubricating functions. It should be appreciated that while an alumina/titania mixture is preferred, other mixtures such as alumina/chromia and alumina/zirconia could be utilized.

Figure 6:
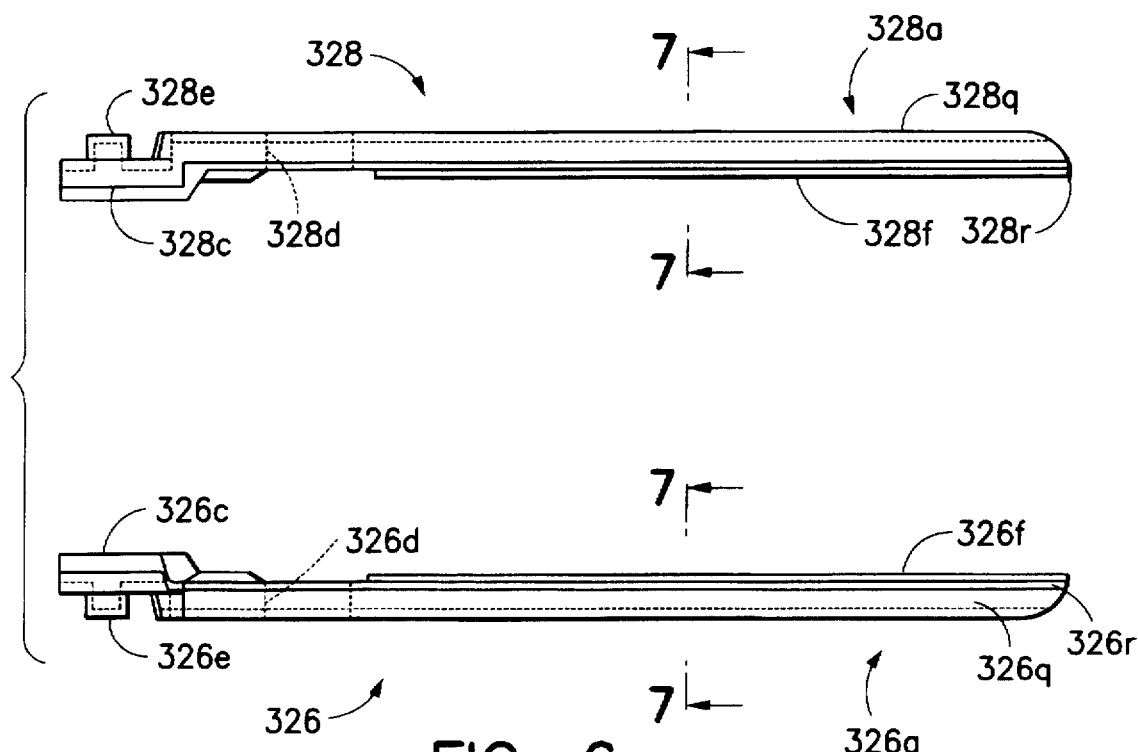
FIG. 6 is a view similar to FIG. 2 of a third embodiment of straight scissor blades according to the invention.
Figure 7:
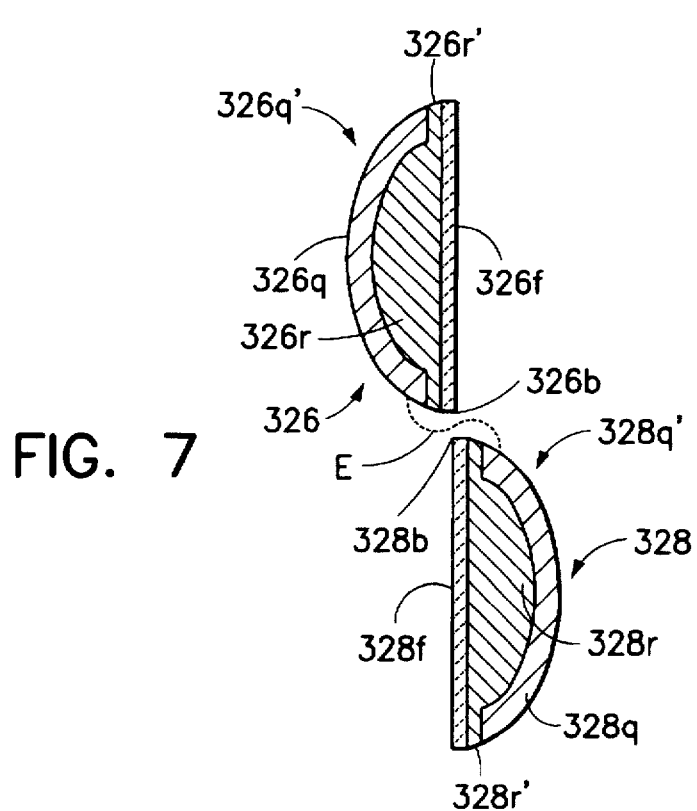
FIG. 7 is a cross sectional view of the scissor blades of FIG. 6 taken along lines 7—7 and shown in their operating positions.

FIGS. 6 and 7 show a third embodiment of straight scissor blades 326, 328. According to this embodiment, both scissor blades 326 and 328 are laminated assemblies which include a blade support 326q', 328q', which itself is a laminated sub-assembly of a non-conductive core support 326r, 328r and an outer metallic layer support 326q, 328q. A titanium dioxide layer or face 326f, 320f defining a shearing surface is coated on the inner surface of the non-conductive core 326r, 328r. It will be appreciated that the blades 326, 328 are preferably provided with sharpened opposed cutting edges 326b, 328b. The outer metallic layers 326q, 328q of the blade supports 326q', 328q' form the electrode portions of the blades through which cautery current is applied. As seen best in FIG. 6, the outer metallic layers 326q, 328q extend along substantially the entire length of the blades (over the non-conductive cores 326r, 328r) to make an electrical connection with a source of cautery at the proximal connecting lugs 326e, 328e of the blades. As seen in FIG. 7, the path of preferential current flow "E" is through the electrode portions 326q, 328q of the blades which are insulated from the cutting edges and the shearing surfaces of the blades. Because of this arrangement, cautery current may be applied continuously throughout the cutting procedure since the contact of the shearing surfaces of the blades will not short circuit the device.

The embodiment shown in FIGS. 6 and 7 may be manufactured by molding ceramic cores 326r, 328r and laminating the outer conductive surfaces 326q, 328q with metal by gluing, sputtering, metalizing, thermal spraying, plating, etc. the metal layers onto the ceramic cores. The inner faces of titanium dioxide 326f are applied as described above. In this case, the ceramic material should preferably be formed (although not necessarily formed) with a flange type cross section as denoted by 326r', 328r' so that the outer metal laminates do not come too close to the $TiO_2$ inner faces as the titanium dioxide ceramic is not a very good insulator. According to the presently preferred embodiment, the outer layers may be formed from a metal such as copper, gold, stainless steel, superalloy, or other conducting material. The ceramic cores 326r, 328r may be made of alumina, zirconia, or other suitable ceramic.

It will be appreciated that either of the blades 326, 328 from FIGS. 6 and 7 may be used with an opposed blade 26, 28, 226, 228 from FIGS. 2, 3, and 5, or with a conventional blade 128 from FIG. 4 as explained above with reference to FIG. 4.

Figures 8, 9:
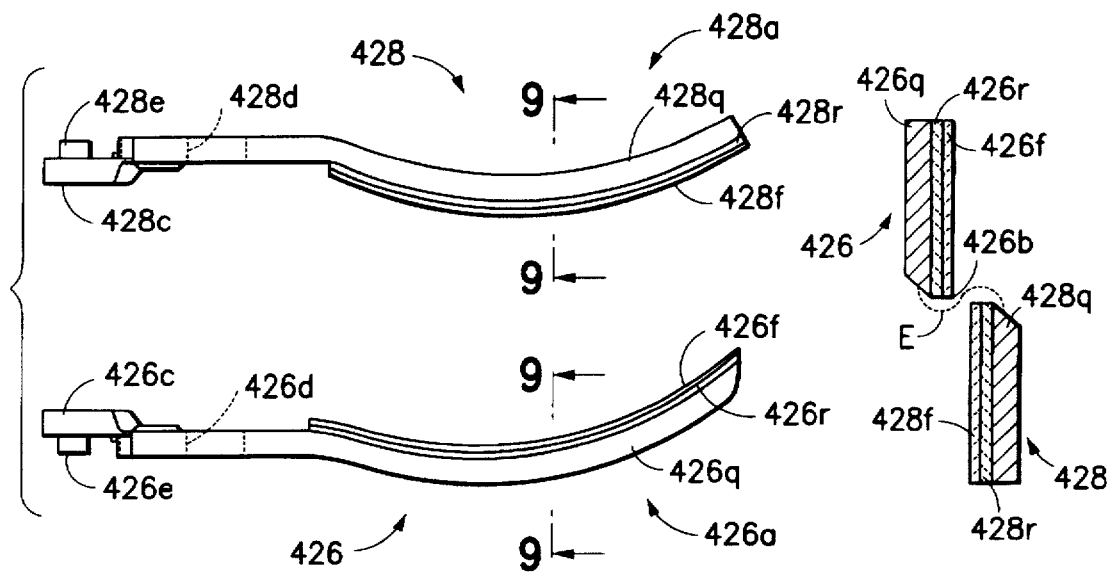
FIG. 8 is a view similar to FIGS. 2 and 6 of the first embodiment of curved scissor blades according to the invention.
FIG. 9 is a cross sectional view of the scissor blades of FIG. 8 taken along lines 9—9 and shown in their operating positions.
Figures 10, 11:
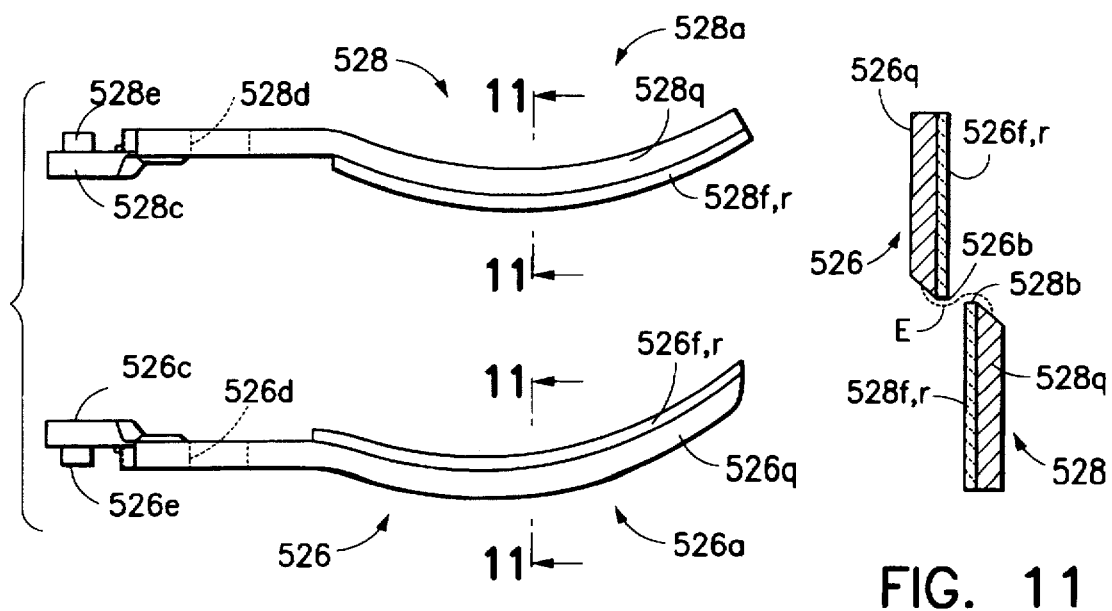
FIG. 10 is a view similar to FIG. 8 of the second embodiment of curved scissor blades according to the invention.
FIG. 11 is a cross sectional view of the scissor blades of FIG. 10 taken along lines 11—11 and shown in their operating positions.
Figure 12:
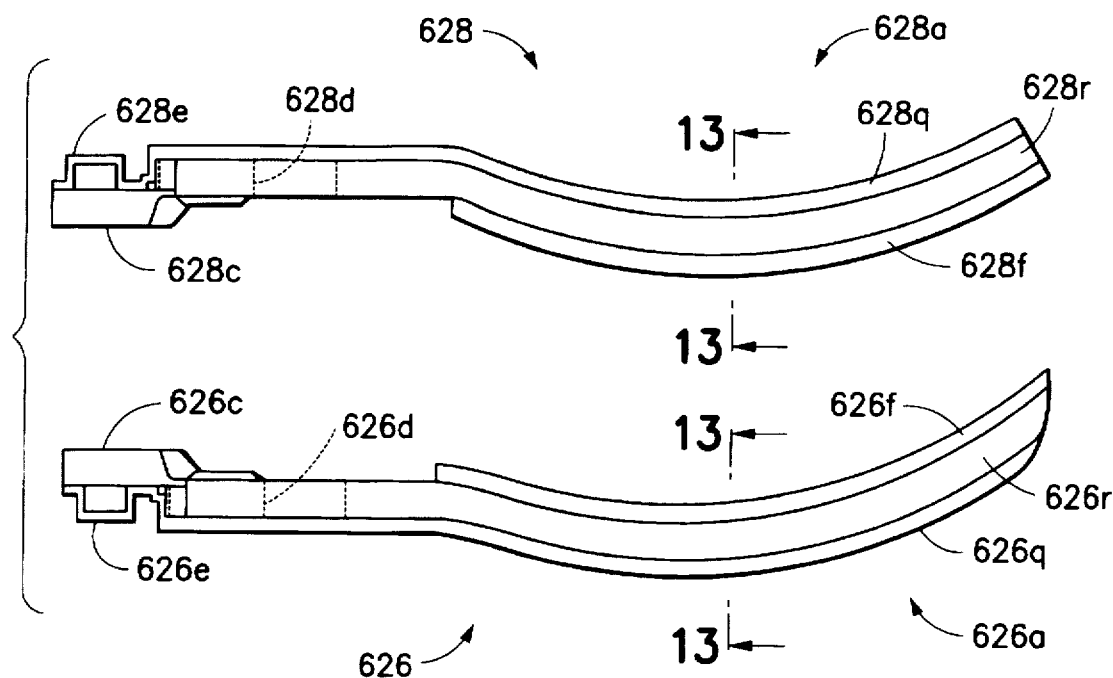
FIG. 12 is a view similar to FIGS. 8 and 10 of the third embodiment of curved scissor blades according to the invention.
Figure 13:
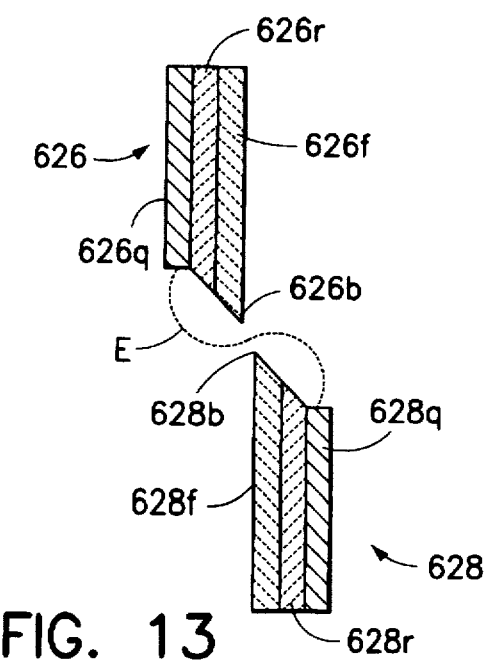
FIG. 13 is a cross sectional view of the scissor blades of FIG. 12 taken along lines 13—13 and shown in their operating positions.
Figure 14:
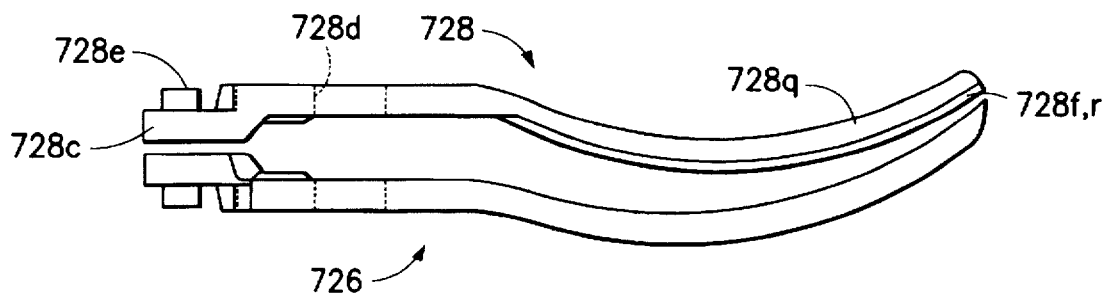
FIG. 14 is a view similar to FIGS. 8, 10, and 12 of scissor blades according to the invention where one of the blades has layers which are not coextensive.
Figure 15:
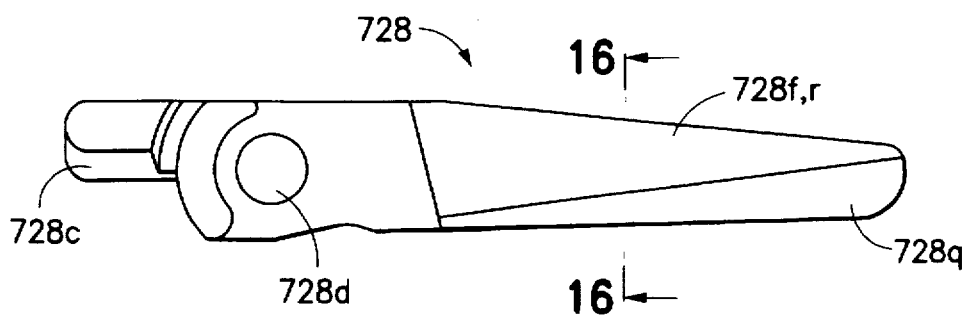
FIG. 15 is a side elevation view of the layered blade of FIG. 14.

As mentioned above, the invention may be used in conjunction with straight scissor blades or curved scissor blades. FIGS. 8–13 show the three embodiments of the invention described above, but in the context of curved scissor blades. Each of the first scissor blades 426, 526, 626 in FIGS. 8—13 has a curved distal portion 426a, 526a, 626a, a lower proximal tang 426c, 526a, 626a and a mounting hole 426d, 526d, 626d therebetween. A connecting lug 426e, 526e, 626e extends orthogonally outward from the surface of the tang 426c, 526c, 626c in a first direction. As shown in FIGS. 9, 11, and 13, the distal portion 426a, 526a, 626a includes a lower cutting edge 426b, 526b, 626b and an inner or shearing surface 426f, 526f, 626f. Behind the inner surface 426f, 526f, 626f of the first scissor blade is an insulating layer 426r, 526r, 626r, and a conducting electrode layer 426q, 526q, 626q. The opposed second scissor blade 428, 528, 628 is configured similarly to the first scissor blade and has a curved distal portion 428a, 528a, 628a, an upper proximal tang 428c, 528c, 628c, and a mounting hole 428d, 528d, 628d therebetween. A connecting lug 428e, 528e, 628e extends orthogonally from the surface of the tang 428c, 528c, 628c in a second direction which is opposite to the first direction mentioned above with regard to the first scissor blade 426, 526, 626. The distal portion 428a, 528a, 628a includes a upper cutting edge 428b, 528a, 628a and an inner surface 428f, 528f, 628f. Behind the inner surface 428f, 528f, 628f of the second scissor blade 428, 528, 628 is an insulating layer 428r, 528r, 628r, and a conducting electrode layer 428q, 528q, 628q.

The embodiment of FIGS. 8 and 9 is substantially the same as the embodiment of FIGS. 2 and 3, except for the curvature of the blades 426, 428. The embodiment of FIGS. 10 and 11 is substantially the same as the embodiment of FIG. 5, except for the curvature of the blades 526, 528. The embodiment of FIGS. 12 and 13 is substantially the same as the embodiment of FIGS. 6 and 7, except for the curvature of the blades 626, 628.

Figures 16A, 16B, 16C:
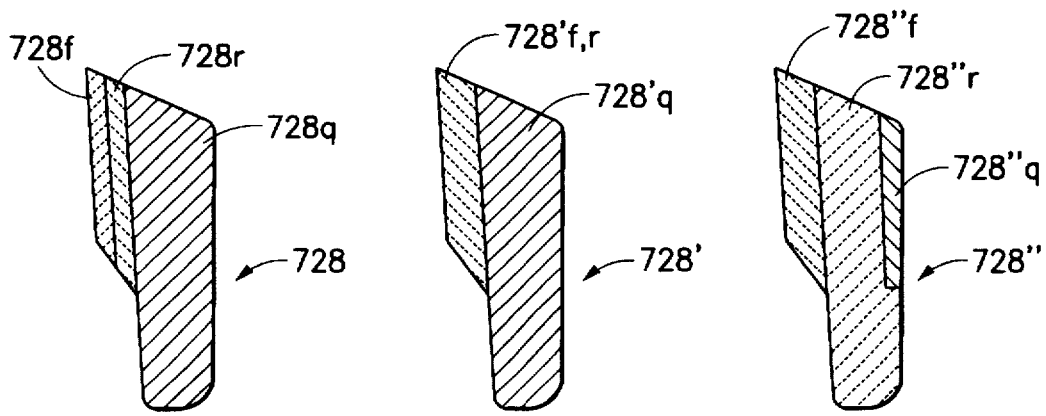
FIG. 16a is a cross sectional view of the blade of FIG. 15, as taken along line 16—16, and according to the first embodiment of the invention.
FIG. 16b is a cross sectional view of the blade of FIG. 15, as taken along line 16—16, and according to the second embodiment of the invention.
FIG. 16c is a cross sectional view of the blade of FIG. 15, as taken along line 16—16, and according to the third embodiment of the invention.

Turning now to FIGS. 14, 15, and 16a–16c, the layered scissor blades according to the invention may include layers having different surface areas. For example, the blade 728 seen in FIGS. 14, 15, and 16a, may be provided as a conductive layer 728q with an insulative layer 728r and a face layer 728f where the insulative layer and the face layer do not cover the entire facing surface of the conductive layer 728q. The blade 728 thus shown in FIG. 16a is manufactured according to the first embodiment of the invention where the conductive layer 728*q* is a metallic blade support and the insulative and face layers 728*r*, 728*f* are applied separately. However, as shown in FIG. 16*a*, the layers 728*f* and 728*r* are not coextensive with the conductive layer 728*q*, either horizontally or vertically. FIG. 16*b* shows this type of arrangement with a blade 728' while using the mixture of insulative and face layers 728'*f,r* as described above with reference to the second presently preferred embodiment of the invention. FIG. 16*c* shows a blade 728" which is manufactured according to the third embodiment of the invention described above, but where the conductive layer 728"q and the face layer 728"f are not coextensive with the insulative layer 728"r. Additional information about layered scissor blades having layers which are not coextensive is found in copending application Ser. No. 08/377,156 which has been incorporated herein by reference.

There have been described and illustrated herein several embodiments of bipolar endoscopic surgical scissor blades and an instrument incorporating them. While particular embodiments of the invention have been described, it is invention be that the invention be limited thereto, as it is intended that the invention be as broad in scope as the art will allow and that the specification be read likewise. Thus, while particular conductive and non-conductive materials have been disclosed, it will be appreciated that other materials could be utilized. Also, while blades of specific shape and dimension have been shown, it will be recognized that blades having different shapes and dimensions could be used with similar results obtained. While means for pivotally joining the blades has been shown as an axle screw with a nut, other pivotal joining means could be used. For example, a clevis with an integral axle pin, or a snap-in axle pin, or a riveted axle pin could all be used. While means for supplying each blade with a voltage has been shown as a bipolar push rod, it will be appreciated that other means such as a bipolar clevis and bipolar hollow tube could be used. Individual shielded electrical conductors within the hollow tube could also be used for this purpose. In addition, while the electrical coupling of the conductive portion of each blade has been shown as the proximal connecting lug which connects to a link, it will be appreciated that an electrical coupling could be made through a two piece bipolar clevis axle. Also, while the means for imparting scissor-like movement to the blades has been shown as a push rod, a pull wire or other reciprocating arrangement might be used as well. In addition, while the means for coupling the scissor blades to the push rod has been shown as an orthogonal lug, it will be understood that other means such as a connecting hole could be used while achieving substantially the same results. Moreover, while particular methods have been disclosed in reference to laminating conductive and non-conductive layers, it will be appreciated that other methods could be used as well.

We claim:

1. A bipolar electrosurgical instrument for cutting and coagulating tissue comprising:
    a) first and second blade members each comprising a laminated assembly of an outer electrically conductive layer and an inner face layer comprising an element selected from the group consisting of titanium dioxide and chromium dioxide, said inner face layer forming a shearing surface of said blade member;
    b) means for pivotally joining said first and second blade members together with their respective shearing surfaces facing one another;
    c) means coupled to at least one of said first and second blade members for imparting a scissors-like movement relative to the other of said first and second blade members; and
    d) means for applying a voltage between the outer electrically conductive layers of said first and second blade members.

2. A bipolar electrosurgical instrument according to claim 1, wherein:
    each of said first and second blade members further comprises an intermediate electrically insulative layer between said outer electrically conductive layer and said inner face layer.

3. A bipolar electrosurgical instrument according to claim 2, wherein:
    said intermediate electrically insulative layer is a ceramic.

4. A bipolar electrosurgical instrument according to claim 3, wherein:
    said intermediate electrically insulative layer is alumina.

5. A bipolar electrosurgical instrument according to claim 2, wherein:
    said inner face layer comprises titanium dioxide.

6. A bipolar electrosurgical instrument according to claim 2, wherein:
    said outer conductive layer is applied to said intermediate electrically insulative layer by one of gluing, sputtering, metalizing, thermal spraying, and plating.

7. A bipolar electrosurgical instrument according to claim 2, wherein:
    said outer conductive layer and said intermediate electrically insulative layer are not coextensive.

8. A bipolar electrosurgical instrument according to claim 1, wherein:
    said inner face layer comprises a mixture of a ceramic and said element selected from the group consisting of titanium dioxide and chromium dioxide.

9. A bipolar electrosurgical instrument according to claim 8, wherein:
    said ceramic is alumina.

10. A bipolar electrosurgical instrument according to claim 9, wherein:
    said inner face layer comprises a mixture of alumina and titanium dioxide in a ratio by weight of between 75/25 and 95/5 of said alumina to said titanium dioxide.

11. A bipolar electrosurgical instrument according to claim 10, wherein:
    said ratio is approximately 87/13 of said alumina to said titanium dioxide.

12. A bipolar electrosurgical instrument according to claim 1, wherein:
    said shearing surfaces of said first and second blade members are curved.

13. A bipolar electrosurgical instrument according to claim 1, wherein:
    said outer conductive layer is stainless steel.

14. A bipolar electrosurgical instrument according to claim 1, wherein:
    said outer conductive layer and said inner face layer are not coextensive.

15. A bipolar electrosurgical instrument for cutting and coagulating tissue, comprising:
    a) first and second blade members each having an inner shearing surface and a conductive portion, at least one of said blade members comprising a laminated assembly of an outer electrically conductive layer and an inner face layer comprising an element selected from the group consisting of titanium dioxide and chromium dioxide, and defining said inner shearing surface;

b) means for pivotally joining said first and second blade members with their respective inner shearing surfaces facing one another;

c) means coupled to at least one of said first and second blade members for imparting a scissors-like movement relative to the other of said first and second blade members; and d) means for applying a voltage between said conductive portions of said first and second blade members.

16. A bipolar electrosurgical instrument according to claim 15, wherein:

said at least one of said blade members further comprises an intermediate electrically insulative layer between said outer electrically conductive layer and said inner face layer.

17. A bipolar electrosurgical instrument according to claim 16, wherein:

said intermediate electrically insulative layer is a ceramic.

18. A bipolar electrosurgical instrument according to claim 17, wherein:

said intermediate electrically insulative layer is alumina.

19. A bipolar electrosurgical instrument according to claim 16, wherein:

said inner face layer comprises titanium dioxide.

20. A bipolar electrosurgical instrument according to claim 16, wherein:

said outer conductive layer is applied to said intermediate electrically insulative layer by one of gluing, sputtering, metalizing, thermal spraying, and plating.

21. A bipolar electrosurgical instrument according to claim 16, wherein:

said outer conductive layer and said intermediate electrically insulative layer are not coextensive.

22. A bipolar electrosurgical instrument according to claim 15, wherein:

said inner face layer comprises a mixture of a ceramic and said element selected from the group consisting of titanium dioxide and chromium dioxide.

23. A bipolar electrosurgical instrument according to claim 22, wherein:

said ceramic is alumina.

24. A bipolar electrosurgical instrument according to claim 23, wherein:

said inner face layer comprises a mixture of alumina and titanium dioxide in a ratio by weight of between 75/25 and 95/5 of said alumina to said titanium dioxide.

25. A bipolar electrosurgical instrument according to claim 24, wherein:

said ratio is approximately 87/13 of said alumina to said titanium dioxide.

26. A bipolar electrosurgical instrument according to claim 15, wherein:

said shearing surfaces of said first and second blade members are curved.

27. A bipolar electrosurgical instrument according to claim 15, wherein:

said outer conductive layer is stainless steel.

28. A bipolar electrosurgical instrument according to claim 15, wherein:

said outer conductive layer and said inner face layer are not coextensive.

29. An endoscopic scissor blade for use in a bipolar endoscopic instrument, said blade comprising:

a) an inner face layer comprising an element selected from the group consisting of titanium dioxide and chromium dioxide, and defining an inner shearing surface;

b) an outer electrically conductive layer which is electrically insulated from said inner shearing surface; and d) means for coupling a source of voltage to said outer electrically conductive layer.

30. An endoscopic scissor blade according to claim 29, further comprising:

e) means for pivotally mounting said scissor blade; and f) means for coupling said scissor blade to a means for imparting a pivotal movement to said scissor blade.

31. An endoscopic scissor blade according to claim 29, further comprising:

e) an intermediate electrically insulative layer between said outer electrically conductive layer and said inner face layer.

32. An endoscopic scissor blade according to claim 31, wherein:

said intermediate electrically insulative layer is a ceramic.

33. An endoscopic scissor blade according to claim 32, wherein:

said intermediate electrically insulative layer is alumina.

34. An endoscopic scissor blade according to claim 31, wherein:

said inner face layer comprises titanium dioxide.

35. A bipolar electrosurgical instrument according to claim 31, wherein:

said outer conductive layer is applied to said intermediate electrically insulative layer by one of gluing, sputtering, metalizing, thermal spraying, and plating.

36. An endoscopic scissor blade according to claim 31, wherein:

said outer conductive layer and said intermediate electrically insulative layer are not coextensive.

37. An endoscopic scissor blade according to claim 29, wherein:

said inner face layer comprises a mixture of a ceramic and said element selected from the group consisting of titanium dioxide and chromium dioxide.

38. An endoscopic scissor blade according to claim 37, wherein:

said ceramic is alumina.

39. An endoscopic scissor blade according to claim 38, wherein:

said inner face layer comprises a mixture of alumina and titanium dioxide in a ratio by weight of between 75/25 and 95/5 of said alumina to said titanium dioxide.

40. A bipolar electrosurgical instrument according to claim 39, wherein:

said ratio is approximately 87/13 of said alumina to said titanium dioxide.

41. An endoscopic scissor blade according to claim 29, wherein:

said inner shearing surface is curved.

42. An endoscopic scissor blade according to claim 29, wherein:

said outer conductive layer is stainless steel.

43. An endoscopic scissor blade according to claim 29, wherein:

said outer conductive layer and said inner face layer are not coextensive.

* * * * *